(12) United States Patent
Lee

(10) Patent No.: US 8,926,487 B2
(45) Date of Patent: Jan. 6, 2015

(54) METHOD OF SEPARATING FREE OIL FROM FAT

(76) Inventor: Hee Young Lee, Seoul (KR)

( * ) Notice: Subject to any disclaimer, the term of this patent is extended or adjusted under 35 U.S.C. 154(b) by 0 days.

(21) Appl. No.: 12/885,918

(22) Filed: Sep. 20, 2010

(65) Prior Publication Data

US 2011/0309037 A1  Dec. 22, 2011

Related U.S. Application Data

(63) Continuation of application No. 10/595,572, filed as application No. PCT/KR2005/001965 on Jun. 23, 2005, now Pat. No. 7,819,846.

(30) Foreign Application Priority Data

Jun. 23, 2004 (KR) .................. 10-2004-0047260

(51) Int. Cl.
*A61M 5/165* (2006.01)
*A61M 5/145* (2006.01)
*A61B 10/02* (2006.01)
*A61B 17/00* (2006.01)
*A61M 5/315* (2006.01)
*A61M 5/31* (2006.01)

(52) U.S. Cl.
CPC .......... *A61M 5/14566* (2013.01); *A61M 5/165* (2013.01); *A61B 10/0283* (2013.01); *A61B 2017/00761* (2013.01); *A61B 2017/00969* (2013.01); *A61M 5/31511* (2013.01); *A61M 2005/3128* (2013.01)
USPC ............. 494/37; 210/781; 210/350; 604/190; 604/231; 604/542

(58) Field of Classification Search
USPC ........... 210/780–782, 350; 604/190, 231, 542
See application file for complete search history.

(56) References Cited

U.S. PATENT DOCUMENTS 3,891,553 A * 6/1975 Ayres ............................ 210/789
(Continued)

FOREIGN PATENT DOCUMENTS

JP    2002-126083 A    5/2002
KR    20-0327374 Y1    9/2003

OTHER PUBLICATIONS

European Office Action, dated Apr. 28, 2011, Appln. No. 05 765 282.8-2319.

(Continued)

*Primary Examiner* — Timothy Cleveland
(74) *Attorney, Agent, or Firm* — Ladas & Parry LLP

(57) ABSTRACT

A syringe piston used in fat transplantation is structured such that free oil is easily separated from suctioned fat by a syringe piston having a filter and naturally discharged through the rear side thereof. The syringe piston without a shaft, used in fat transplantation, disposed in a syringe-shaped cylindrical vessel, includes a piston body without the shaft, a packing coupled with an outer surface of the piston body to seal between the piston body and the syringe-shaped cylindrical vessel, a free oil discharging hole communicated with the front side and the rear side of the piston body, an opening and closing device for opening and closing the free oil discharging hole, and a filtering device disposed in a passage through which free oil is discharged to filter fat and pass the free oil.

11 Claims, 15 Drawing Sheets

(56) References Cited

U.S. PATENT DOCUMENTS

| | | | |
|---|---|---|---|
| 3,894,952 A | 7/1975 | Ayres | |
| 3,897,337 A | 7/1975 | Ayres | |
| 4,753,634 A | 6/1988 | Johnson | |
| 5,354,483 A | 10/1994 | Furse | |
| 5,549,816 A * | 8/1996 | Harp et al. | 422/513 |
| 7,195,610 B1 * | 3/2007 | Flachbart | 604/99.01 |
| 2004/0251217 A1 * | 12/2004 | Leach et al. | 494/37 |
| 2005/0124073 A1 * | 6/2005 | Freund | 494/43 |
| 2005/0261620 A1 * | 11/2005 | Ballin | 210/782 |

OTHER PUBLICATIONS

European Office Action dated Nov. 13, 2012, Appln. No. 05 765 828.8-2319.
Supplementary European Search Report; Appln. No. EP 05 76 5828 dated Jun. 16, 2010.
Written Opinion of the International Searching Authority, mailed Sep. 26, 2005, International Application No. PCT/KR2005/001965.
International Search Report; mailed Sep. 26, 2005, PCT/KR2005/001965.

* cited by examiner

METHOD OF SEPARATING FREE OIL FROM FAT

CROSS-REFERENCE TO RELATED PATENT APPLICATION

This application is a continuation of U.S. patent application Ser. No. 10/595,572, filed on Apr. 27, 2006, in the Korean Intellectual Property Office, which claims the benefit of the International Application No. PCT/KR2005/001965, filed on Jun. 23, 2005, in the World Intellectual Property Office, the disclosures of which are incorporated herein in its entirety by reference.

BACKGROUND OF THE INVENTION

1. Field of the Invention

The present invention relates to a syringe piston used in fat transplantation, and more particularly, to a syringe piston used in fat transplantation in which free oil of fat, sucked by a piston having a filter formed in the syringe piston, is easily separated and automatically discharged through the rear side of the syringe piston.

2. Description of the Related Art

Fat transplantation is a surgical operation performed to fill a space where soft tissues of a patient have ever occupied, and particularly, is performed for cosmetic purposes such as removing wrinkles, dimples, or the like. The worst disadvantage of the fat transplantation is that the transplanted fat is suctioned into the patient and the volume thereof is reduced. If the suctioning force applied to fat during extraction is excessively high, approximately 80% to 90% of the fat cells do not survive transplantation, necessitating that the surgical operation be repeated. Moreover, when the fat is suctioned into the patient, since the dead tissue serves as a source of infection or decomposed material may be toxic, serious scarring may occur or normal skin tissue around the skin into which fat is transplanted may be damaged.

Autologous fat transplantation requires that red blood cells and free oil liberated from ruptured fat cells be removed from the suctioned fat. When a red blood cell is escaped from blood vessel, the red blood cell is decomposed and produces thromboxane A2. The thromboxane A2 serves as an ionized free radical to demolish normal tissues, thereby demolishing fat tissues. Thus, engraftment of the transplanted fat is remarkably reduced.

The free oil is decomposed upon separation from an adipose cell and is ionized into a free fatty acid. The free fatty acid is a free radical, thereby destroying normal tissues and adipose cells. Thus, the free fatty acid reduces the engraftment of the transplanted fat and induces cell death, which in turn leads to secondary inflammation or serves as a culture medium of bacteria. Moreover, the free oil, remaining between the adipose cell wall and the adipose cell, serves as a capsule and disturbs oxygen supply essential to the survival of the transplanted adipose tissues. Accordingly, free oil is one of the principle reasons for death of transplanted adipose tissue.

For this reason, although the free oil must be removed prior to the fat transplantation, some of the free oil is transplanted and causes trouble. Particularly, when a great deal of fat is transplanted, the free oil accumulates below the transplant area, thereby causing inflammation or tissue death, or enlarging granulomata that is touched like a tumor.

According to the conventional art, in order to remove red blood cells and the free oil, the following methods are used. The first is the most primitive and involves storing suctioned fat in a funnel-shaped vessel until red blood cells and the free oil are separated from the sucked fat. As time passes, blood, bodily fluids, and pure fat layers are gradually formed in turn from the bottom of the sucked fat, and impurities such as the blood and bodily fluids are removed until the pure fat is tinged with light yellow. However, it is difficult to separate the free oil via the above-mentioned method, and it takes a long period of time.

The second method involves wrapping the sucked fat with a cloth and squeezing the cloth by hand to separated impurities from the sucked fat. When squeezing the wrapped fat, the sucked fat is pressed and the free oil can be separated from the sucked fat, and the cloth functions as a filter for filtering various impurities. However, this method is disadvantageous in that it takes a great deal of time to separate free oil, the separation procedure is complicated, and, above all, there is a risk that the separated free oil may be infected due to the contact with air.

A third method involves suctioning fat into a syringe type vessel and separating the free oil via density gradient centrifugation. After the density gradient centrifugation of the sucked fat, red blood layer is positioned at the lowest layer and is clearly distinguished from other components. The free oil forms the supernatant such that the free oil is positioned above the adipose cell layer and forms an emulsion with the adipose cell layer. In order to remove the red blood cells, since pressure must be applied from the upper side of the syringe type vessel, the upper free oil may be mixed with the pure fat again. Thus, the free oil must be separated in the first place such that a syringe needle is inserted into the highest layer to extract only the free oil, or a piston or cap is removed from the syringe vessel and the syringe type vessel is turned upside down such that the free oil is immediately discharged from the syringe type vessel. Next, when only the pure fat is positioned on the highest layer, pressure is applied to the upper portion of the syringe type vessel to press the fat and to discharge the red blood. However, the former step needs a lot of time and manpower, and the latter has risks such as inflammation due to contact with air and loss of the pure fat.

Therefore, since, in the above-mentioned methods, it is difficult to simultaneously separate the red blood having the highest specific gravity and the free oil having the lowest specific gravity from the sucked fat, the procedures are complicated and inflammation occurs upon transplantation. Particularly, since the free oil is not effectively separated, the desired volume substitution cannot be effected.

The fourth method uses a piston having a syringe type vessel without a shaft. The piston, invented by this inventor, has a piston head of a syringe used in fat transplantation having a filter for passing air and water and for filtering fat (Korea Registered Utility Model No. 0327374). During the suction of fat by external pneumatic pressure, air and water are removed from the sucked fat, and water and free oil contained in the sucked fat are filtered from the sucked fat by pressing the sucked fat. The above syringe piston uses the conventional syringe type vessel and the external pneumatic pressure to remarkably enhance fat suction efficiency. According to the syringe piston, fat can be pressed without the density gradient centrifugation, the fat is hardly infected when contacting external air during the treatment of the fat, and the red blood and the free oil can be effectively removed in comparison with the above-mentioned methods. However, some of free oil or red blood cells contained in the sucked fat may remain in the syringe used in the fat transplantation during the pressing. Moreover, if the pressure or the suction force is not properly and accurately controlled, adipose cells may be discharged from the syringe used in the fat transplantation. Additionally, since the syringe used in the fat transplantation has a structure wherein bodily fluids such as free oil is passed through the filter by external pneumatic pressure, the filter is formed with fine holes of about 5 μm to 50 μm so that the filter may be easily clogged. Moreover, when the filter is very fine and accurately formed, the adipose cells can be prevented from being discharged from the syringe used in the fat transplantation.

SUMMARY OF THE INVENTION

Therefore, the present invention has been made in view of the above problems, and it is an object of the present invention to provide a syringe piston having a filtering device of a syringe used in fat transplantation in which free oil contained in fat sucked by the piston is easily separated by density gradient centrifugation and automatically discharged through the rear side of the syringe piston so that the free oil is accurately removed without loss of the extracted adipose cells, risk of contamination or inflammation is reduced, and engraftment of transplanted fat is increased.

In accordance with an aspect of the present invention, the above and other objects can be accomplished by the provision of a syringe piston without a shaft, used in fat transplantation, disposed in a syringe-shaped cylindrical vessel, including a piston body without the shaft, a packing coupled with an outer surface of the piston body to form a seal between the piston body and the syringe-shaped cylindrical vessel, a free oil discharging hole communicated with the front side and the rear side of the piston body, an opening and closing device for opening and closing the free oil discharging hole, and a filtering device disposed in a passage through which free oil is discharged to filter fat and pass the free oil.

Preferably, the syringe piston further includes a weight for increasing a total weight of the syringe piston.

The filtering device has a net filter having a pore diameter of 10 μm to 100 μm.

The free oil discharging hole includes a plurality of holes penetrating the front end of the piston body and the rear end of the piston body, and the opening and closing device includes a packing for covering the rear end of the piston body, and a closing screw for fixing the packing.

The filtering device includes a cap for sealing the front side of the free oil discharging hole, an outer filtering circumference disposed in the piston body to maintain a predetermined gap between the piston body and the inner circumference of the cylindrical vessel such that fat is filtered and the free oil passes therethrough, and a through-hole formed between the outer filtering circumference and the packing and communicated between the free oil discharging hole of the piston body and the cap.

The free oil discharging hole has a single central hole penetrating the front end of the piston body and the rear end of the piston body, and the opening and closing device for opening and closing the free oil discharging hole includes first and second check valves disposed at the sides of the free oil discharging hole and operated by the external force, and first and second fixing covers having through-holes formed at the central portions to fix the first and second check valves to the piston body.

Since the procedure of separating free oil from the sucked fat is very simple, manpower can be reduced, the free oil is perfectly separated without loss of extracted adipose cells, contamination, and inflammation, and engraftment of fat can be enhanced. Therefore, a great deal of fat can be transplanted using the syringe piston of the present invention and the syringe piston is effectively used in plastic surgery requiring a great deal of volume substitute such as breast enlargement.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The preferred embodiments of the present invention will be described in detail with reference to the accompanying drawings.

Figure 1:
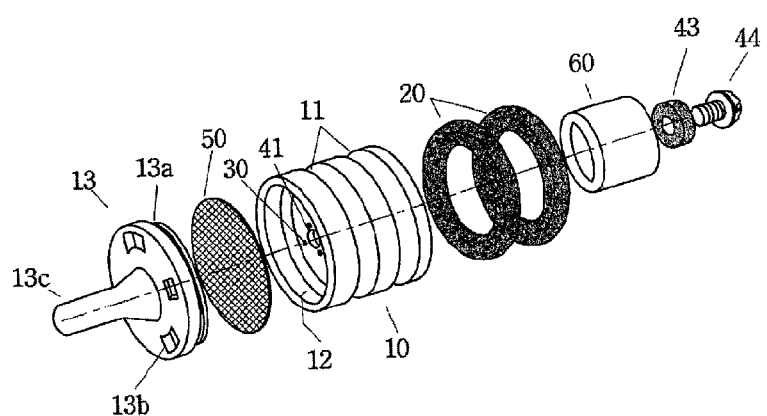
FIG. 1 is an exploded perspective view illustrating a syringe piston used in fat transplantation according to a first preferred embodiment of the present invention.
Figure 2:
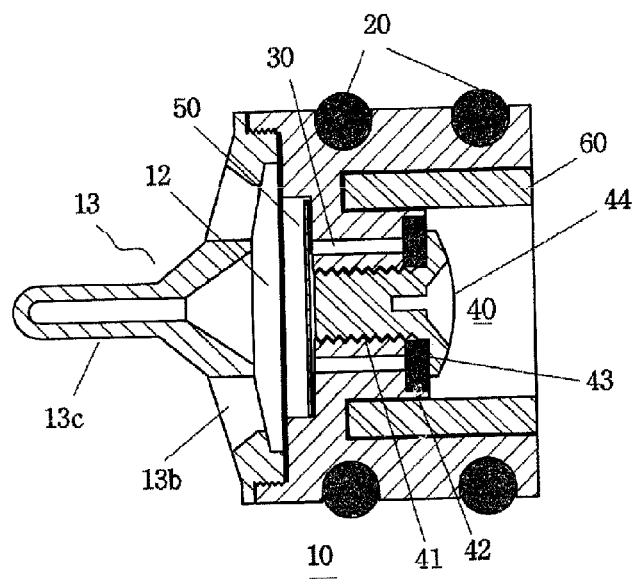
FIG. 2 is a sectional view of an assembly of the syringe piston according to the first preferred embodiment of the present invention.
Figure 3:
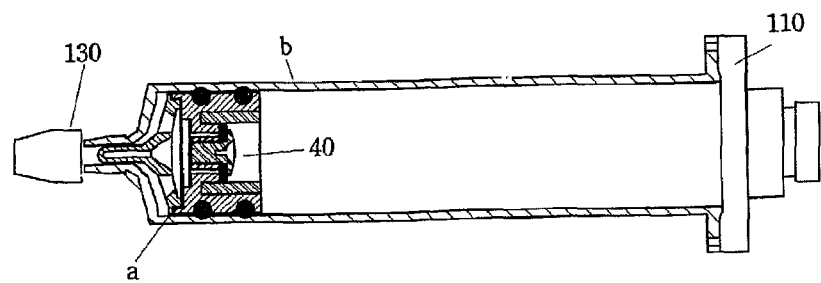
FIG. 3 is a sectional view illustrating the syringe piston according to the first preferred embodiment of the present invention coupled with a vessel.

FIG. 1 is an exploded perspective view illustrating a syringe piston used in fat transplantation according to a first preferred embodiment of the present invention, FIG. 2 is a sectional view of an assembly of the syringe piston according to the first preferred embodiment of the present invention, and FIG. 3 is a sectional view illustrating the syringe piston according to the first preferred embodiment of the present invention coupled with a vessel. The syringe piston a used in fat transplantation according to the first preferred embodiment of the present invention includes a piston body 10 without a shaft, a packing 20 coupled with the outer surface of the piston body 10 to form a seal between a cylindrical vessel b and the piston body 10, a free oil discharging hole 30 for communicating the front side with the rear side of the piston body 10, an opening and closing device 40 for opening and closing the free oil discharging hole 30, a filtering device formed in a free oil discharging passage, and a weight 60 coupled with the rear side of the piston body 10. All the elements of the syringe piston according to the first preferred embodiment of the present invention are made of non-toxic materials.

The cylindrical vessel b is structured such that suction of fat and the transplantation of fat are performed in the cylindrical vessel in the state of preventing the fat from contacting air. The cylindrical vessel b has a syringe shape and a rear cap 110 coupled with the rear side of the cylindrical vessel b to close the rear side of the cylindrical vessel b. The rear cap 110 is connected to an external pneumatic unit. The cylindrical vessel b has also a cannular 100 attached to the front side of the cylindrical vessel b and inserted into the patient to suck and inject fat. A front cap 130 is attached to the front side of the cylindrical vessel b to close the cannular 100 so as to prevent substances contained in the cylindrical vessel b from leaking.

The piston body 10 of the syringe piston moves forward and rearward to suck and discharge fat while closely contacting the inner wall of the cylindrical vessel b and has no a shaft. Negative pressure and positive pressure, supplied by the external pneumatic unit connected to the rear cap 110 of the cylindrical vessel b, function like a shaft.

Moreover, the piston body 10 has a cylindrical shape and is made of synthetic resin to have two ring grooves 11 formed in the outer circumference with which the packings 20 are coupled. The packings 20 are conventional packings such as a rubber ring, a silicon ring. The ring-shaped packings 20 are inserted into the grooves 11 formed in the piston body 10 so as to form a seal between the syringe piston a and the cylindrical vessel b.

The filtering device includes a circular net type filter 50 having holes of the size for filtering adipose cells and passing the free oil. The filter 50 passes the free oil and filters adipose cells when the density gradient centrifugation is performed so that pure fat can be obtained. The filter 50 passes only free oil to the rear side of the cylindrical vessel b when the red blood and the free oil form layers in the cylindrical vessel b so that the free oil is separated from the fat.

Preferably, the size of the holes of the filter 50 is about 10 μm to 100 μm. Since the free oil infiltrates and passes through the filter 50 due to the difference of specific gravities during the density gradient centrifugation, the filter 50 may comprise a thick filter or several layers of filters having large holes of about 100 μm, or by a single layer or a few layers of net filters having small holes of about 50 μm.

Additionally, the piston body 10 has a filter groove 12, formed in the front end of the piston body 10, into which the filter 50 is inserted. Threads are formed in the inner circumference of the filter groove 12 and a cap 13 is coupled with the threads. Thus, when manufacturing or using the syringe piston, according to the use of the syringe piston or conditions, the filter 50 can be easily replaced so that a user can select the pore size.

The cap 13 has a disc shape and is coupled with the filter groove 12 by a thread 13 a formed in the outer circumference of the cap 13. The cap 13 has a plurality of through-holes 13 b through which the sucked fat passes, and a protrusion 13 c, corresponding to the shape of the front end of the cylindrical vessel b, formed in the front side thereof. The size of the through-holes 13 b is sufficient to prevent fat tissues from damage when the fat passes the through-holes 13 b.

Since the cap 13 is coupled with the filter groove 12 by means of the thread, the filter can be conveniently replaced with a filter required by a user or an orderer when manufacturing or using the syringe piston a. Moreover, the protrusion 13 c formed in the front end prevents gaps such that the front end of the syringe piston a is engaged with the front end of the cylindrical vessel b when the syringe piston a is coupled with the cylindrical vessel b. Thus, when sucking fat, the protrusion 13 c prevents highly compressible air from remaining in the cylindrical vessel b so that suction efficiency is increased. When injecting fat, the protrusion 13 c pushes the fat in the cylindrical vessel b to the end so that loss of the fat can be minimized.

In this embodiment, the free oil discharging hole 30 is a passage through which the free oil passing through the filter 50 is separated from adipose cells and moves to the rear side of the syringe piston a in the cylindrical vessel b. the free oil discharging hole 30 includes four holes penetrating the filter groove 12 formed in the front end of the piston body 10 and the rear side of the piston body 10.

The opening and closing device 40 for opening and closing the free oil discharging hole 30 closes the free oil discharging hole 30 when suctioning fat from the patient or injecting the suctioned fat in the cylindrical vessel b into the patient so that the negative or positive pressure is applied to the syringe piston a from the external pneumatic unit, and opens the free oil discharging hole 30 when the density gradient centrifugation is performed so that the free oil passed through the filter 50 is discharged to the rear side of the cylindrical vessel b.

The opening and closing device 40 for opening and closing the free oil discharging hole 30 may be structured such that, when the cylindrical vessel b is filled with bodily fluids, the free oil discharging hole 30 is safely opened and closed by external manipulation without risk of contamination.

The opening and closing device 40 of the first preferred embodiment of the present invention includes a screw hole 41 formed in the central portion of the piston body 10, the free oil discharging hole 30 formed around the screw hole 41, a packing groove 42 formed in the rear side of the piston body 10 and covering the free oil discharging hole 30 such that an annular packing 43 is hung on a closing screw 44 and the closing screw 44 is fastened into the screw hole 41 so that the free oil discharging hole 30 can be opened and closed.

The free oil discharging hole 30 and the opening and closing device 40 prevent pressure from leaking by fastening the closing screw 44 to the end when suctioning and injecting fat, and allow the free oil perfectly escapes a space between the free oil discharging hole 30 and the packing 43 by slightly releasing the closing screw 44. When fastening and releasing the closing screw 44, a long screwdriver is used. When the outer wall of the cylindrical vessel b where the syringe piston a is positioned is pressed, the closing screw 44 is fastened or released so that the free oil discharging hole 30 is easily opened and closed in the state that the cylindrical vessel b is filled with fat.

Figure 4:
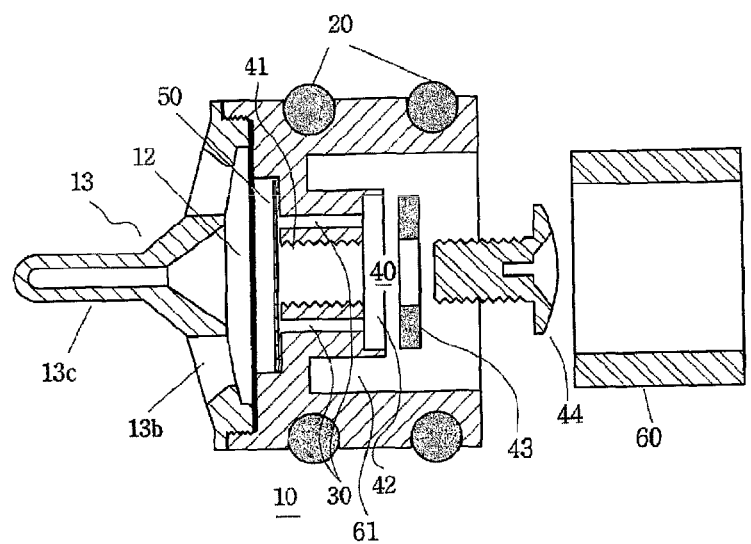
FIG. 4 is an exploded sectional view of main parts of the syringe piston according to the first preferred embodiment of the present invention.

The weight 60 presses fat when the density gradient centrifugation is performed so that the separation of the free oil is enhanced. The weight 60 may be structured such that the syringe piston a is made of heavy material and serves as the weight, and as shown in FIG. 4, an annular groove 61 is formed in the circumference of the packing groove 42 into which the packing 43 of the rear side of the syringe piston a is inserted and a ring-shaped weight 60 is coupled with the annular groove 61. During the density gradient centrifugation, the syringe piston a moves smoothly forward due to the weight 60 to press fat, thereby smoothly discharging the free oil.

Figure 5:
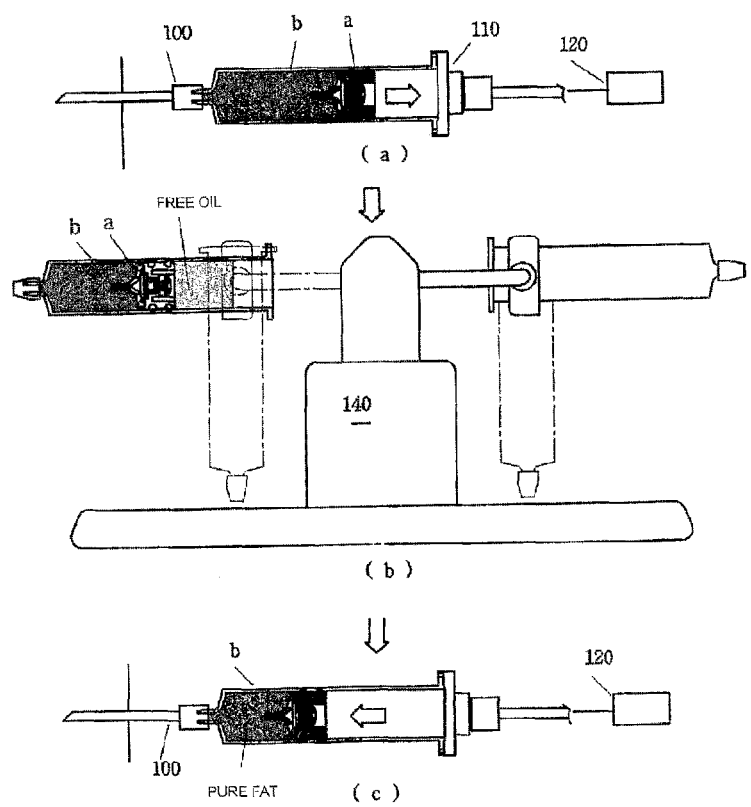
FIG. 5 is a view illustrating suction, separation, and transplantation of fat according to the preferred embodiment of the present invention.

The suction of fat, the separation of pure fat, and fat transplantation are described with reference to FIG. 5 as follows.

[Suction of Fat]

The cannular 100 is coupled with the front end of the cylindrical vessel b and the syringe piston a is positioned in the cylindrical vessel b while closing the closing screw 44 to perfectly close the free oil discharging hole 30. Next, the rear side of the cylindrical vessel b is closed by the rear cap 110 and the rear cap 110 is connected to the external pneumatic unit 120 so as to push the syringe piston a to the front end of the cylindrical vessel b using positive pressure. The cannular 100 is inserted into the patient and negative pressure is applied to the rear space of the syringe piston a such that the fat extracted from the patient is accommodated in the front space of the syringe piston a (See FIG. 5 a).

[Separation of Pure Fat]

After completion of fat suction, the front cap 130 is attached to the front end of the cylindrical vessel b instead of the cannular 100 (See FIG. 3), the rear cap 110 is detached, and the closing screw 44 is released to open the free oil discharging hole 30. When the cylindrical vessel b is inserted into a centrifugal separator 140 and the density gradient centrifugation is performed, mixture of blood and bodily fluids and fat components are separated in turn due to specific gravity difference. During the density gradient centrifugation, the fat components occupy the upper layer of the cylindrical vessel b, adipose cells in the fat components are filtered by the filter 50 of the syringe piston a, and the free oil passes through the filter 50 and is naturally discharged through the rear side of the syringe piston a. When the weight 60 is additionally coupled with the syringe piston a, the weight 60 moves the syringe piston a forward to press the fat, thereby discharging the free oil. The cylindrical vessel b is turned upside down to completely remove the free oil, the closing screw 44 is fastened to close the free oil discharging hole 30, and the rear cap 110 is re-coupled with the rear side of the syringe piston a. Next, the front cap 130 of the front end of the cylindrical vessel b is removed, the external pneumatic unit 120 is connected to the rear cap 110 to gradually apply positive pressure to the rear side of the syringe piston a so that blood and bodily fluids are extracted and discharged and only the pure fat remains in the front space of the syringe piston a (FIG. 5 b).

The centrifugal separator 140, depicted in the drawings, is a centrifugal 10 separator having a swing-out type rotor in which the cylindrical vessel b is arranged upright when the swing-out rotor is stopped and is horizontally arranged when the swing-out rotor is rotated.

[Fat Transplantation]

The cannular 100, coupled with the front end of the cylindrical vessel b, is inserted into a desired portion of the patient and tile pure fat is injected into the patient by applying positive pressure to the rear space of the syringe piston a or transferring the pure fat to other type syringe and using the other type syringe.

Figure 6:
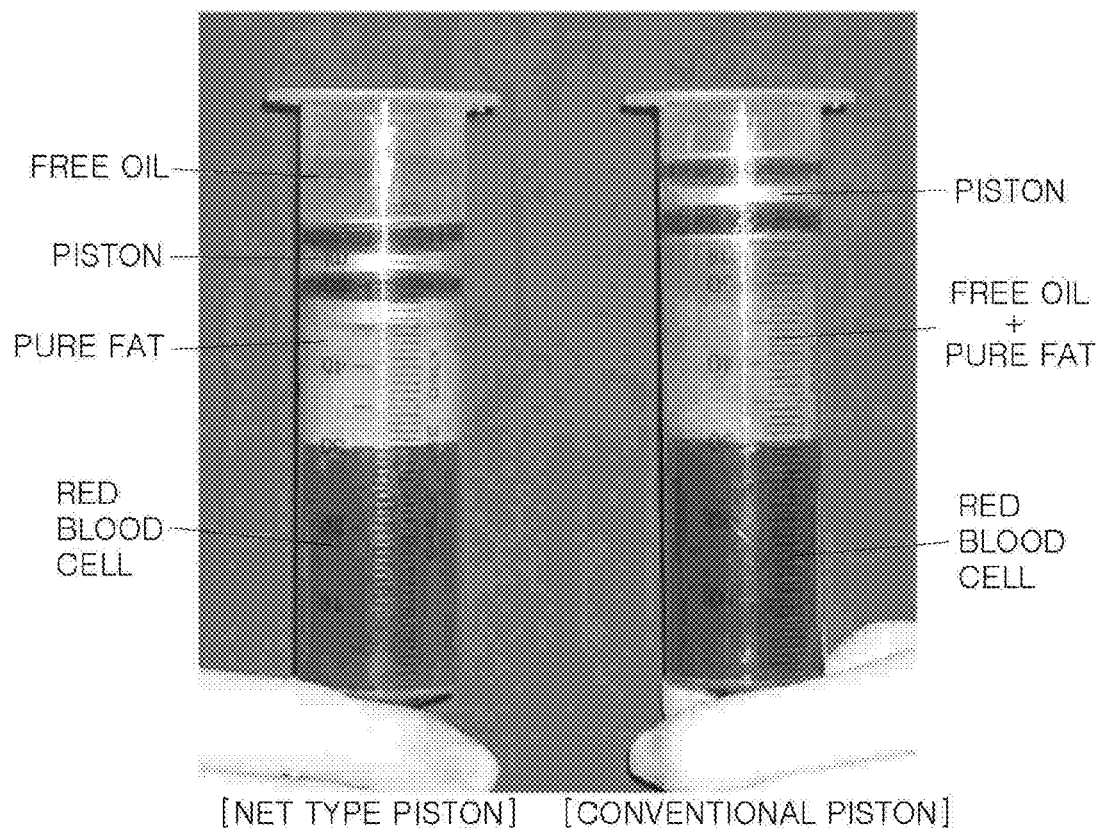
FIG. 6 is a view illustrating examples, in which fats are suctioned by the 5 syringe piston according to the preferred embodiment of the present invention and a conventional syringe piston and density gradient centrifugation is performed.

FIG. 6 is a photograph for comparison of an example of the density gradient centrifugation using the syringe piston a according to the present invention and an example of the density gradient centrifugation using a conventional syringe piston, respectively applied to a syringe-shaped vessel having a capacity of 60 cc. In the drawing, the photograph on the left, labeled <net type piston>, indicates the result of using the syringe piston according to the present invention and the photograph on the right, labeled <conventional piston>, indicates the result of using the conventional syringe piston. The syringe piston according to the present invention, applied to the above-mentioned example, is structured such that a syringe piston (about 8.5 g including a net filter), in which a single net filter, made of stainless steel (SUS 304) and having holes of 60 µm diameter, is inserted into the filter groove, four free oil discharging holes of 2 mm diameter are formed around the screw hole, and a ring-shaped weight (about 13 g) is attached to the syringe piston, thereby total weight is 21.5 g. The conventional syringe piston has no hole through which the free oil passes and a shaft is removed. The above examples show result that same quantity of fat is extracted from the patient using pneumatic pressure and the density gradient centrifugation is performed at 5000 rpm. As can be seen from the examples, in the example using the conventional syringe piston, red blood is positioned in the lowest layer in the vessel and a mixture layer of free oil and fat is formed in the highest layer in the vessel. However, in the example using the syringe piston according to the present invention, the syringe piston is positioned between the free oil layer and the fat layer so that the fat layer is clearly distinguished from the free oil layer.

The result may be caused by the facts that adipose cells and free oil of low specific gravities are separated from the red blood layer and are pushed to the rotation center of the centrifugal separator such that adipose cells are filtered and restricted and the free oil naturally passes through the filter and moves to the outer side of the syringe piston, whereby adipose cells and the free oil are separated from fat, simultaneously, the syringe piston moves forward due to the centrifugal force to press adipose cells and push free oil remained in the adipose cells rearward so that the free oil is separated from fat. During the performance of the density gradient centrifugation in this process, the weight moves the syringe piston forward so that fat is further pressed and free oil more easily separated.

Figure 7:
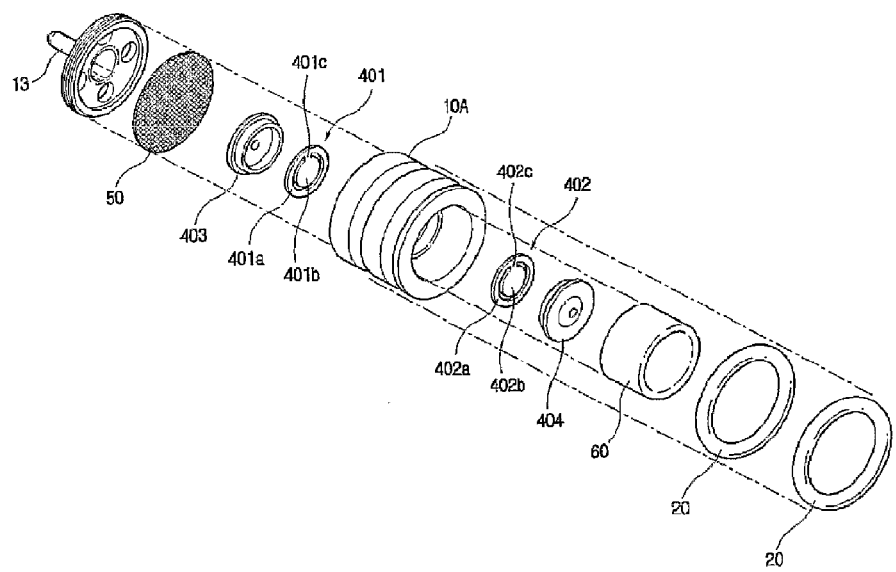
FIG. 7 is an exploded perspective view illustrating a syringe piston used in fat transplantation according to a second preferred embodiment of the present invention.
Figure 8:
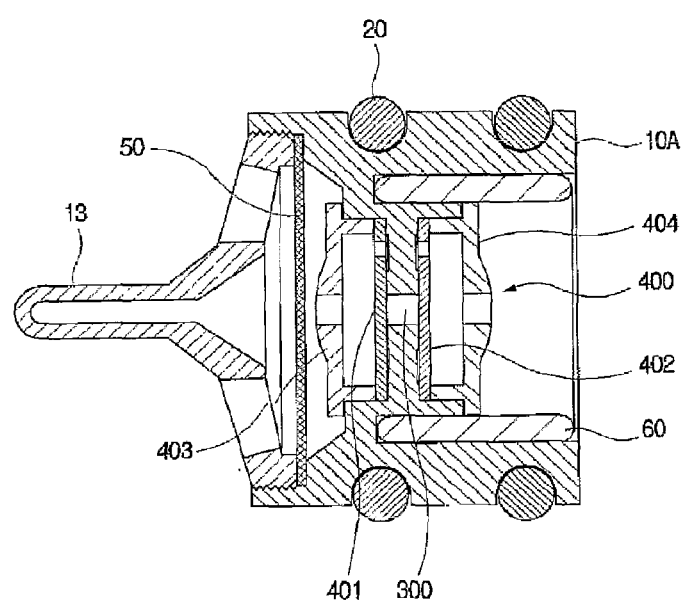
FIG. 8 is a sectional view of an assembly of the syringe piston according to the second preferred embodiment of the present invention.
Figure 9:
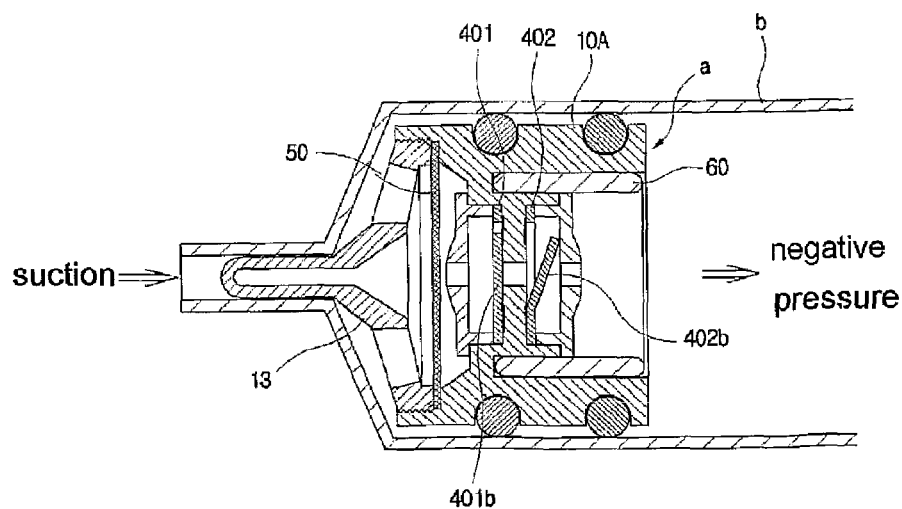
FIGS. 9 to 11 are views illustrating operation of the syringe piston according to the second preferred embodiment of the present invention.
Figure 10:
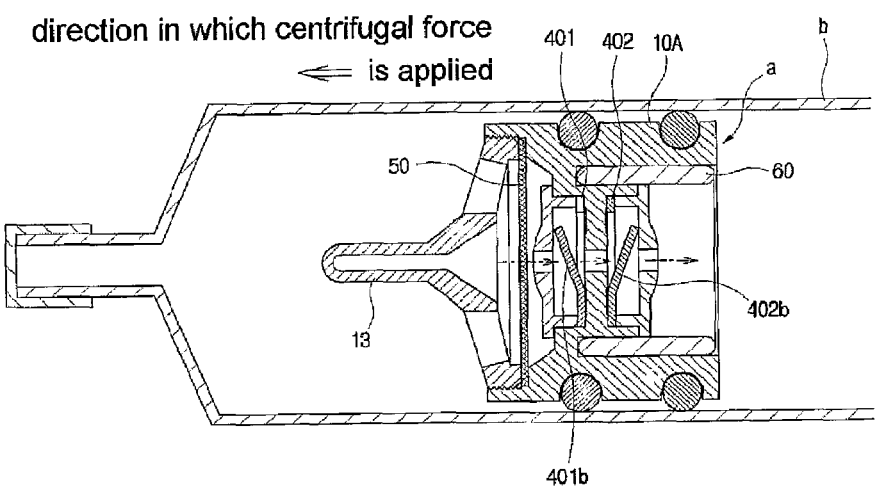
Figure 11:
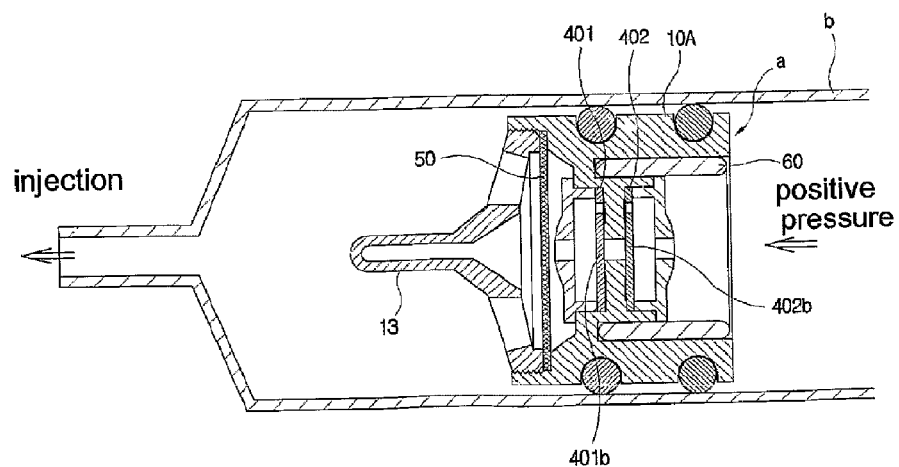

FIGS. 7 and 8 are views illustrating a syringe piston used in fat transplantation according to a second preferred embodiment of the present invention, and FIGS. 9 to 11 are views illustrating operation of the syringe piston according to the second preferred embodiment of the present invention. The syringe piston according to the second preferred embodiment of the present invention is different from the syringe piston according to the first preferred embodiment of the present invention in view of a free oil discharging hole 300 for communicating the front side and the rear side of a piston body 10A and an opening and closing device 400 for opening and closing the free oil discharging hole 300 and their operation. Therefore, like numerals are assigned to like elements and the description for structure and operation will be omitted.

In the second preferred embodiment of the present invention, the free oil discharging hole 300 includes a single central hole penetrating the front end and the rear end of the piston body 10A. The opening and closing device 400 for opening and closing the free oil discharging hole 300 includes first and second thin plate check valves 401 and 402 disposed at the sides of the free oil discharging hole 300 and operated to open and close the free oil discharging hole 300 by the external force, first and second fixing covers 403 and 404 respectively having through-holes formed in the centers thereof and fixing the first and second check valves 401 and 402 in the piston body 10A.

The first and second check valves 401 and 402, as shown in FIG. 7, include rims 401 *a* and 402 *a* fixed to the piston body 10A by the fixing covers 403 and 404, and opening and closing parts 401 *b* and 402 *b*, having a size sufficient to open and close the free oil discharging hole 300, in which the rims 401 *a* and 402 *a* are connected to parts of the opening and closing parts 401 *b* and 402 *b* by connectors 401 *c* and 402 *c*. The opening and closing parts 401 *b* and 402 *b* are supported by the connectors 401 *c* and 402 *c* and are easily deformed by the external force so that the free oil discharging hole 300 is easily opened and closed. The syringe piston according to the second preferred embodiment of the present invention, like the syringe piston according to the first preferred embodiment of the present invention, can perform the suction of fat, the separation of the pure fat, and the fat transplantation. In the suction of fat, as shown in FIG. 9, when negative pressure is formed in the rear space of the syringe piston a, the opening and closing part 402 *b* of the second check valve 402 disposed at the rear side is spaced apart from the free oil discharging hole 300 and is opened due to the negative pressure. In other words, during the suction of fat, when the negative pressure is formed in the rear space as shown in FIG. 9, the opening and closing part 402 *b* of the second check valve 402, disposed at the rear side, is spaced apart from the free oil discharging hole 300 and is opened.

However, the opening and closing part 401 *b* of the check valve 401, disposed at the front side, further closely contacts the free oil discharging hole 300 due to the negative pressure formed in the rear space and closes the free oil discharging hole 300. As a result, the syringe piston a moves to the rear space of the cylindrical vessel b so that fat sucked from the patient is accommodated in the front space of the syringe piston a.

Moreover, the separation of pure fat using the centrifugal separator 140 (See FIG. 5 *b*) after completion of the suction of fat, as shown in FIG. 10, is performed such that the opening and closing part 401 *b* of the first check valve 401, disposed at the front side, is deformed in the direction where the centrifugal force is applied due to the centrifugal force of the centrifugal separator 140 and is away from the free oil discharging hole 300 and opens the free oil discharging hole 300.

At the same time, the weight 60 presses the syringe piston a due to the centrifugal force such that fat positioned in the front space is pressed so that the free oil enters the free oil discharging hole 300. The opening and closing part 402 *b* of the second check valve 402, disposed at the rear side, is pushed back and is opened by the free oil entering the free oil discharging hole 300 so that the first and second check valves 401 *b* and 402 *b* are opened. Therefore, the free oil can be discharged through the free oil discharging hole 300 to the rear space of the syringe piston a.

Due to the difference of specific gravity, the fat in the cylindrical vessel b is separated to blood+bodily fluids, and pure components in turn, and the fat components occupy the highest layer of the cylindrical vessel b during the density gradient centrifugation. Adipose cells among the fat components are filtered by the filter 50 of the syringe piston a and the free oil passes through the filter 50 and is discharged through the free oil discharging hole 300 to the rear side.

Moreover, the fat transplantation, as shown in FIG. 11, is performed such that, when the positive pressure is applied to the rear space of the syringe piston a, the second check valve 402, disposed at the rear side, further closely contacts the free oil discharging hole 300 due to the positive pressure and closes the free oil discharging hole 300. Thus, the syringe piston a can be moved to the front side using the positive pressure so that fat can be injected into human body and pure fat is transferred to other type syringe and is injected into the patient.

As described above, in the syringe piston according to the second preferred embodiment of the present invention, like in the syringe piston of the first preferred embodiment, the suction of fat, the separation of fat, and the fat transplantation can be performed. Moreover, when performing the processes, since the first and second check valves 401 and 402 are automatically opened and closed, bothersome operations such as fastening and releasing the closing screw 44 can be omitted so that convenient and rapid operation can be performed.

Figure 12:
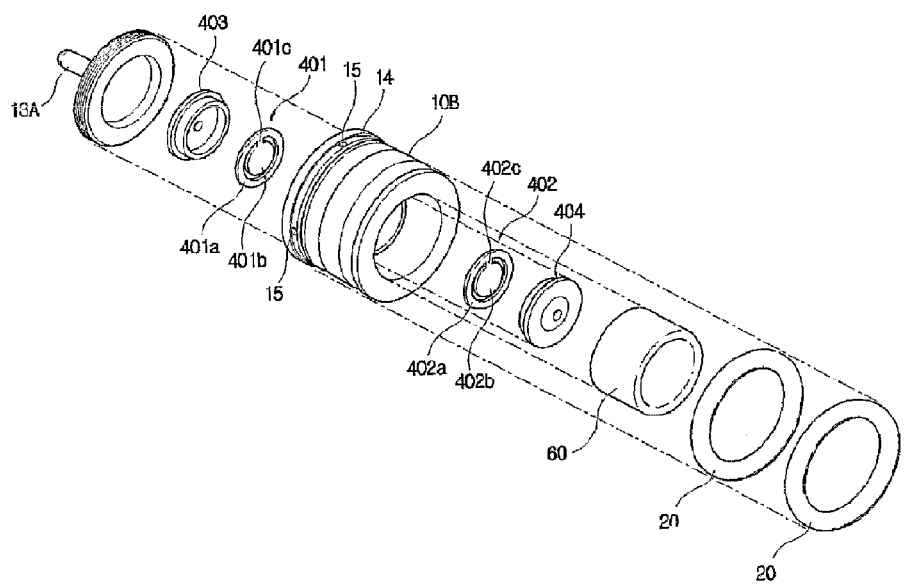
FIG. 12 is an exploded perspective view illustrating a syringe piston used in fat transplantation according to a third preferred embodiment of the present invention.
Figure 13:
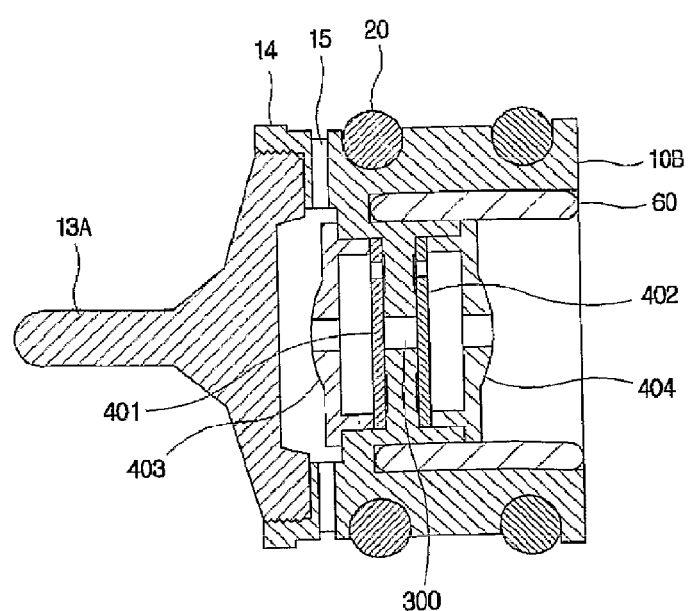
FIG. 13 is a sectional view of an assembly of the syringe piston according to the third preferred embodiment of the present invention.
Figure 14:
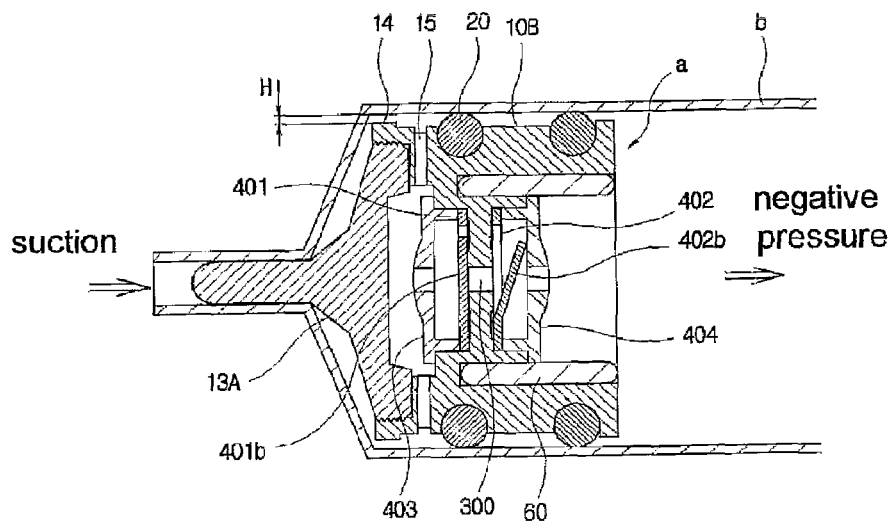
FIGS. 14 to 16 are views illustrating operation of the syringe piston according to the third preferred embodiment of the present invention.
Figure 15:
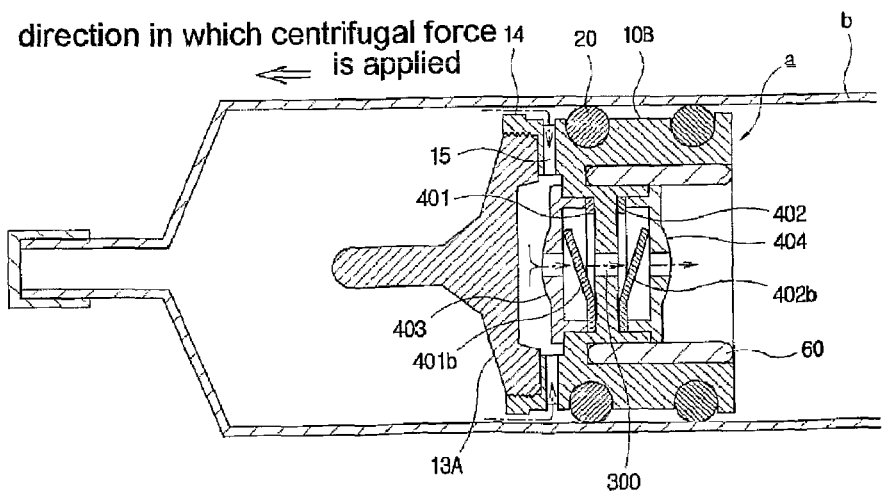
Figure 16:
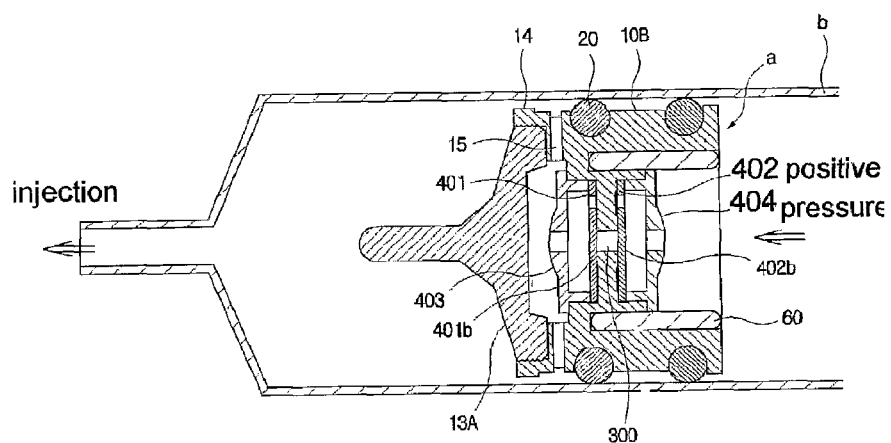

FIGS. 12 and 13 are views illustrating a syringe piston used in fat transplantation according to a third preferred embodiment of the present invention, and FIGS. 14 to 16 are views illustrating operation of the syringe piston according to the third preferred embodiment of the present invention. The syringe piston of the third preferred embodiment is different from the syringe piston of the second preferred embodiment in that an outer filtering circumference 14 is formed to filter fat by maintaining a gap H (See FIG. 14) between a piston body 10B and the inner circumference of the cylindrical vessel b by 10 µm to 199 µm and to pass the free oil, a plurality of through-holes 15 formed between the outer filtering circumference 14 and communicated with the free oil discharging hole 300 of the piston body 10B, a cap 13A has no hole, and a filter is not used, and the structure and operations of other elements of the syringe piston of the third preferred embodiment are identical to those of the syringe piston of the second preferred embodiment. Thus, like numerals are assigned to like elements and the description for structure and operation will be omitted.

According to the syringe piston according to the third preferred embodiment of the present invention, like the first and second preferred embodiments of the present invention, the suction of fat, the separation of pure fat, and the fat transplantation can be performed. In other words, in the suction of fat, as shown in FIG. 14, when negative pressure is formed in the rear space of the syringe piston a, the opening and closing part 402 *b* of the second check valve 402 disposed at the rear side is spaced apart from the free oil discharging hole 300 and is opened due to the negative pressure, but the opening and closing part 401 *b* of the check valve 401, disposed at the front side, further closely contacts the free oil discharging hole 300 due to the negative pressure formed in the rear space and closes the free oil discharging hole 300. As a result, the syringe piston a moves to the rear space of the cylindrical vessel b so that fat sucked from the patient is accommodated in the front space of the syringe piston a.

Moreover, the separation of pure fat using the centrifugal separator 140 (See FIG. 5 *b*) after completion of the suction of fat, as shown in FIG. 15, is performed such that the opening and closing part 401 *b* of the first check valve 401, disposed at the front side, is deformed in the direction where the centrifugal force is applied due to the centrifugal force of the centrifugal separator 140 and is away from the free oil discharging hole 300 and opens the free oil discharging hole 300. At the same time, the weight 60 presses the syringe piston a due to the centrifugal force such that fat positioned in the front space is pressed so that the free oil enters the free oil discharging hole 300. The opening and closing part 402 *b* of the second check valve 402, disposed at the rear side, is pushed back and is opened by the free oil entering the free oil discharging hole 300 so that the first and second check valves 401 *b* and 402 *b* are opened. Therefore, the free oil can be discharged through the free oil discharging hole 300 to the rear space of the syringe piston a.

Due to differences in specific gravity, the fat in the cylindrical vessel b is separated into blood+bodily fluids, and pure components in turn, and the fat components occupy the highest layer of the cylindrical vessel b during the density gradient centrifugation. Adipose cells among the fat components are filtered by the outer filtering circumference 14 of the piston body 10B for maintaining the gap 10 μm to 100 μm between the piston body 10B and the inner circumference of the cylindrical vessel b, and the free oil passes through the outer filtering circumference. The free oil passed through the outer filtering circumference moves to the free oil discharging hole 300 through the through-holes 300 and passes through the free oil discharging hole 400 so that the free oil is naturally discharged to the rear side the syringe piston a.

Moreover, the fat transplantation, as shown in FIG. 16, is performed such that, when the positive pressure is applied to the rear space of the syringe piston a, the second check valve 402, disposed at the rear side, further closely contacts the free oil discharging hole 300 due to the positive pressure and closes the free oil discharging hole 300. Thus, the syringe piston a can be moved to the front side using the positive pressure so that fat can be injected into the patient and pure fat is transferred to other type syringe and injected into the patient.

As described above, in the syringe piston according to the third preferred embodiment of the present invention, like in the syringe pistons of the first and second preferred embodiments, the suction of fat, the separation of fat, and the fat transplantation can be performed. Moreover, when performing the processes, since the first and second check valves 401 and 402 are automatically opened and closed, bothersome operations such as fastening and releasing the closing screw 44 can be omitted so that convenient and rapid operation can be performed.

Additionally, the syringe piston of the third preferred embodiment does not use a filter, unlike the syringe piston of the second preferred embodiment, so that the number of parts is reduced, the costs can be reduced, and the parts of the syringe piston of the third preferred embodiment can be easily assembled into the syringe piston of the third preferred embodiment.

Figure 17:
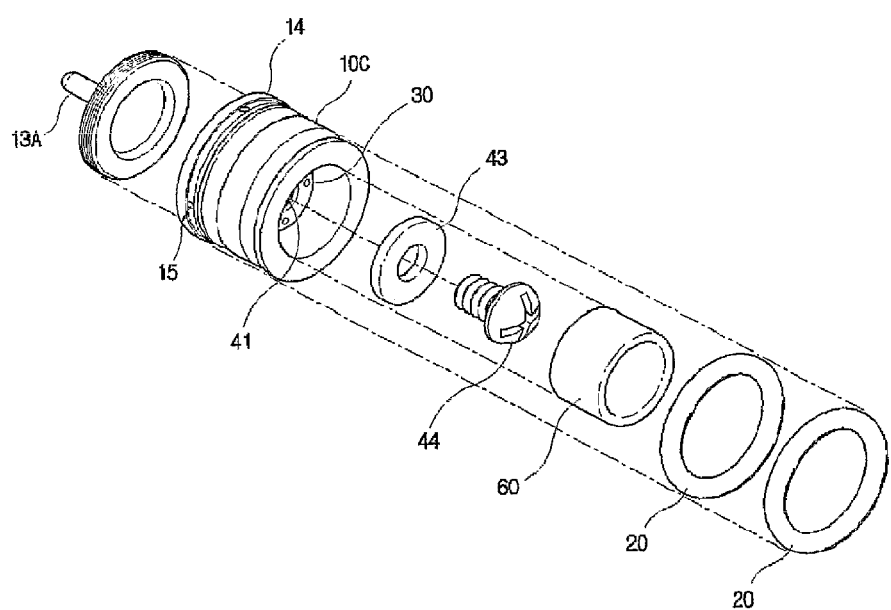
FIG. 17 is an exploded perspective view illustrating a syringe piston used in fat transplantation according to a fourth preferred embodiment of the present invention.
Figure 18:
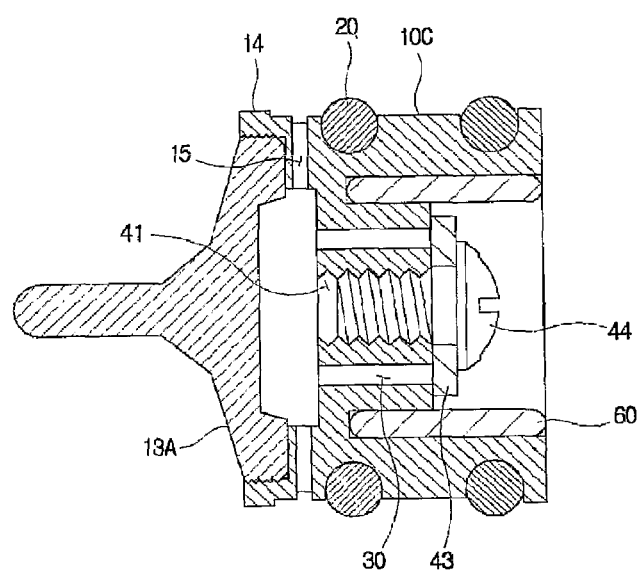
FIG. 18 is a sectional view of an assembly of the syringe piston according to the fourth preferred embodiment of the present invention.
Figure 19:
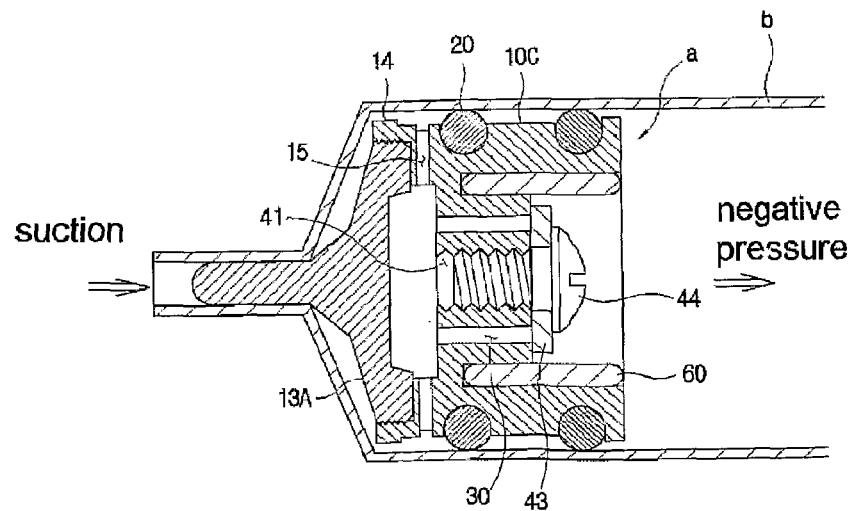
FIGS. 19 to 21 are views illustrating operation of the syringe piston according to the fourth preferred embodiment of the present invention.
Figure 20:
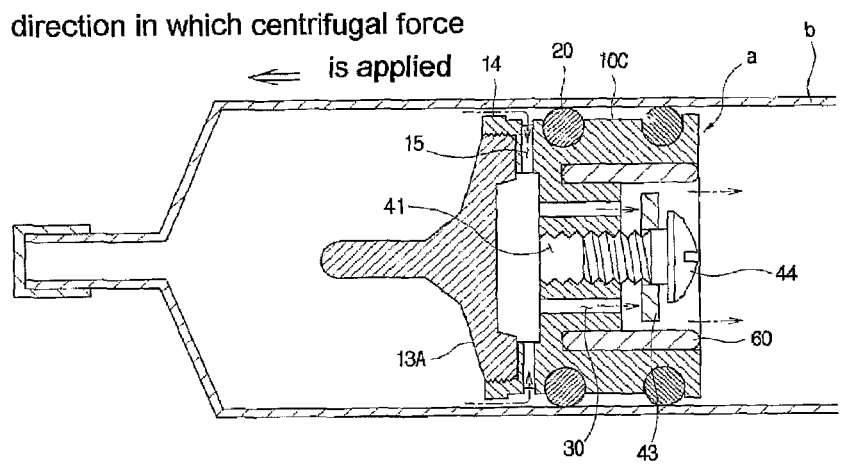
Figure 21:
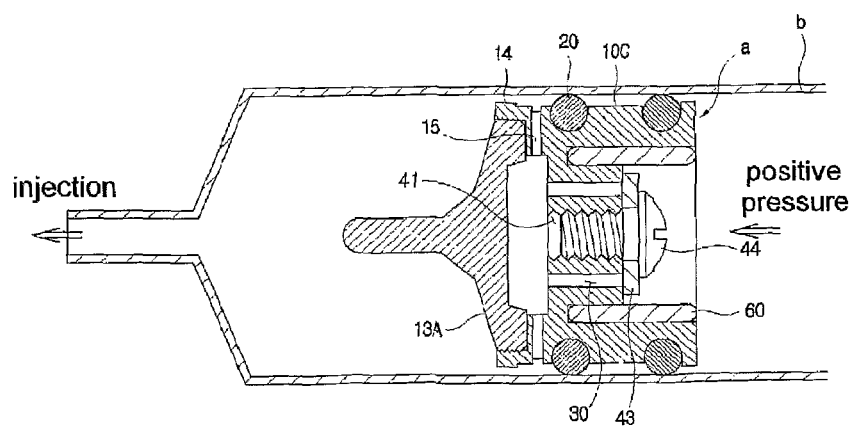

FIGS. 17 and 18 are views illustrating a syringe piston used in fat transplantation according to a fourth preferred embodiment of the present invention, and FIGS. 19 to 21 are views illustrating operation of the syringe piston according to the fourth preferred embodiment of the present invention.

The syringe piston of the fourth preferred embodiment adopts only the free oil discharging hole 30 of a piston body 10C and the opening and closing device 40 of the syringe piston of the first preferred embodiment, and all other elements are the same as those of the syringe piston of the third preferred embodiment. Thus, like numerals are assigned to like elements of the syringe pistons of the first and third preferred embodiments and the description for structure and operation will be omitted.

According to the syringe piston according to the fourth preferred embodiment of the present invention, like the first preferred embodiment to the third preferred embodiment of the present invention, the suction of fat, the separation of pure fat, and the fat transplantation can be performed. In other words, in the suction of fat, as shown in FIG. 19, when negative pressure is formed in the rear space of the syringe piston a by fastening the closing screw 44 such that the free oil discharging hole 30 is closed by the packing 43, the syringe piston a moves to the rear space of the cylindrical vessel b so that fat sucked from the patient is accommodated in the front space of the syringe piston a.

Moreover, the separation of pure fat using the centrifugal separator 140 (See FIG. 5 b) after completion of the suction of fat, as shown in FIG. 20, is performed such that the closing screw 44 is released to form a gap between the packing 43 and the free oil discharging hole 30 so that the free oil discharging hole 30 is opened. In this state, when the centrifugal separator 140 is operated to generate centrifugal force, the weight 60 presses the syringe piston a to the front side due to the centrifugal force and the fat disposed in the front space is pressed. Thus, the free oil is discharged through the opened free oil discharging hole 30 from the front space to the rear space.

Additionally, due to the difference of specific gravity, the fat in the cylindrical vessel b is separated into blood+bodily fluids, and pure components in turn, and the fat components occupy the highest layer of the cylindrical vessel b after density gradient centrifugation. Adipose cells among the fat components are filtered by the outer filtering circumference 14 of the piston body 10C for maintaining the gap 10 μm to 100 μm between the piston body 10C and the inner circumference of the cylindrical vessel b, and the free oil passes through the outer filtering circumference 14. The free oil having passed through the outer filtering circumference 14 moves to the free oil discharging hole 30 through the through-holes 15 and passes through the free oil discharging hole 30 so that the free oil is naturally discharged to the rear side the syringe piston a.

Moreover, in the fat transplantation, as shown in FIG. 21, when the positive pressure is applied to the rear space of the syringe piston a after the free oil discharging hole 30 is closed by fastening the closing screw 44, the syringe piston a can be moved to the front side so that fat can be injected into the patient and pure fat is transferred to other type syringe and injected into the patient.

As describe above, in the syringe piston according to the fourth preferred embodiment of the present invention, like in the syringe pistons of the first to third preferred embodiments, the suction of fat, the separation of fat, and the fat transplantation can be performed. Moreover, in the case of using a shaft having thread meshed with the screw hole 41 of the free oil discharging hole 30 instead of the closing screw 44, the positive or negative pressure is not applied to the rear space of the syringe piston, but a user can directly operate the syringe piston a.

Moreover, since, according to the syringe piston of the fourth preferred embodiment of the present invention, the filter 50 of the syringe piston in the first and second preferred embodiments and the check valves 401 and 402 of the second and third preferred embodiment are not used, the syringe piston of the fourth preferred embodiment is applicable to a small syringe used in the fat transplantation and can be effectively used in a syringe in which it is difficult to apply the negative or positive pressure to the rear space of the syringe piston.

As described above, the syringe piston of the present invention effectively separates free oil from the sucked fat using the syringe piston having a filtering device, and those skilled in the art will appreciate that various modifications, additions and substitutions are possible, without departing from the scope and spirit of the invention.

The syringe piston used in fat transplantation according to the present invention is structured such that the free oil is easily separated from the sucked fat by the syringe piston having a filter and is naturally discharged to the rear side of the syringe piston so that the syringe piston of the present invention is conveniently used in the suction of fat, the separation of pure fat, and the fat transplantation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of separating free oil from fat, which comprises;
    (a) preparing a syringe piston without a shaft, used in fat transplantation, disposed in a syringe-shaped cylindrical vessel, comprising:
    a piston body without the shaft;
    a first packing coupled with an outer surface of the piston body to form a seal between the piston body and the syringe-shaped cylindrical vessel;
    a filter groove formed in a front end of the piston body;
    a number of free oil discharging holes penetrating the piston body so as to provide a path between the filter groove at the front end of the piston body and a rear side of the piston body that is opposite the front side;
    an opening and closing device for opening and closing the free oil discharging holes, the opening and closing device comprising a screw hole formed in a central portion of the piston body adjacent to the free oil discharging holes, and a closing screw fastened into the screw hole so that the free oil discharging holes can be opened and closed;
    a second packing interposed between a head of the closing screw and the free oil discharging holes;
    a filtering device installed in the filter groove and spaced apart from the free oil discharging holes and having a larger cross sectional area than the free oil discharging holes and having holes of the size for filtering fat and passing free oil; and
    a weight coupled to the syringe piston and pressing fat when a density gradient centrifugation is performed so that the separation of the free oil is enhanced;
    (b) closing the free oil discharging hole by closing the closing screw such that the second packing interposed between the head of the screw and the free oil discharging holes seals the free oil discharging holes at the rear side of the piston body;
    (c) sucking fat through a front end of the cylindrical vessel;
    (d) opening the free oil discharging hole by releasing the closing screw;
    (e) performing the density gradient centrifugation of fat during which the weight moves the syringe piston forward towards the front end of the cylindrical vessel to press the fat in order to separate a free oil from the fat.

2. The method of claim 1, wherein the piston body moves by air pressure in the cylindrical vessel.

3. The method of claim 1, wherein the piston body moves toward the front end of the cylindrical vessel when a positive pressure is applied and the piston body moves toward a rear end of the cylindrical vessel when a negative pressure is applied.

4. The method of claim 1, wherein the syringe piston further comprises an annular groove formed in the rear side of the syringe piston, wherein the weight is coupled with the annular groove.

5. The method of claim 1, wherein closing the free oil discharging hole comprising closing the free oil discharging hole with a screwdriver.

6. The method of claim 1, wherein opening the free oil discharging hole comprising opening the free oil discharging hole with a screwdriver.

7. The method of claim 1, wherein the free oil discharging holes are formed around the screw hole.

8. The method of claim 1, further comprising a packing groove formed in the rear end of the piston body and covering the free oil discharging holes, and the free oil discharging holes extend from the packing groove at the read end to the filter groove at the front end, wherein in the step (b) of closing the closing screw, the second packing is disposed within the groove so as to seal the free oil discharging holes.

9. The method of claim 1, wherein the second packing is annular and surrounds and hangs on the closing screw.

10. The method of claim 1, further comprising a cap coupled to the front end of the piston body, the cap comprising a protrusion extending away from the piston body and a plurality of through holes though which fat passes.

11. The method of claim 10, wherein the filter groove comprises first threads formed in the inner circumference of the filter groove, and the cap comprises second threads corresponding to the first threads, and the cap is coupled with the filter groove by the first and second threads.

* * * * *